United States Patent
Otto

(10) Patent No.: US 8,475,535 B2
(45) Date of Patent: Jul. 2, 2013

(54) MULTI-COMPARTMENTAL PROSTHETIC DEVICE WITH PATELLAR COMPONENT TRANSITION

(75) Inventor: Jason Karl Otto, Plantation, FL (US)

(73) Assignee: MAKO Surgical Corp., Ft. Lauderdale, FL (US)

( * ) Notice: Subject to any disclaimer, the term of this patent is extended or adjusted under 35 U.S.C. 154(b) by 439 days.

(21) Appl. No.: 12/397,995

(22) Filed: Mar. 4, 2009

(65) Prior Publication Data

US 2009/0228111 A1 Sep. 10, 2009

Related U.S. Application Data

(60) Provisional application No. 61/068,053, filed on Mar. 4, 2008, provisional application No. 61/068,059, filed on Mar. 4, 2008, provisional application No. 61/194,941, filed on Oct. 2, 2008.

(51) Int. Cl.
*A61F 2/38* (2006.01)

(52) U.S. Cl.
USPC ..................................... 623/20.19; 623/20.31

(58) Field of Classification Search
None
See application file for complete search history.

(56) References Cited

U.S. PATENT DOCUMENTS

| | | |
|---|---|---|
| 2003/0158606 A1 | 8/2003 | Coon et al. |
| 2006/0142657 A1 | 6/2006 | Quaid et al. |
| 2006/0190086 A1 | 8/2006 | Clemow et al. |
| 2008/0058945 A1 | 3/2008 | Hajaj et al. |

FOREIGN PATENT DOCUMENTS

| | | |
|---|---|---|
| EP | 1738720 A2 | 1/2007 |
| FR | 2682287 A1 | 4/1993 |
| WO | WO 2006/020619 A1 | 2/2006 |
| WO | WO 2007/013959 A2 | 2/2007 |
| WO | WO 2007/108933 A1 | 9/2007 |

OTHER PUBLICATIONS

PCT International Search Report corresponding to PCT Application No. PCT/US2009/036041, dated Jul. 16, 2009, 4 pages.
PCT Written Opinion corresponding to PCT Application No. PCT/US2009/036041, dated Jul. 16, 2009, 5 pages.

*Primary Examiner* — David H Willse
*Assistant Examiner* — Javier Blanco
(74) *Attorney, Agent, or Firm* — Foley & Lardner LLP

(57) ABSTRACT

A prosthetic device for forming at least a portion of a joint may have a plurality of segmented components fixed relative to a femur of a body including: a patellofemoral component and a condyle component. Each segmented component may be configured such that a placement at which the segmented component will be fixed relative to the femur is not constrained by a connection to another of the segmented components that is fixed relative to the femur. In an installed configuration, the patellofemoral and condyle components may be fixed relative to the femur such that: a gap is provided between an edge of the patellofemoral component and an opposing edge of the condyle component, and a transition region is provided that extends from a first femoral coronal plane that intersects the patellofemoral component to a second femoral coronal plane that intersects the condyle component.

18 Claims, 13 Drawing Sheets

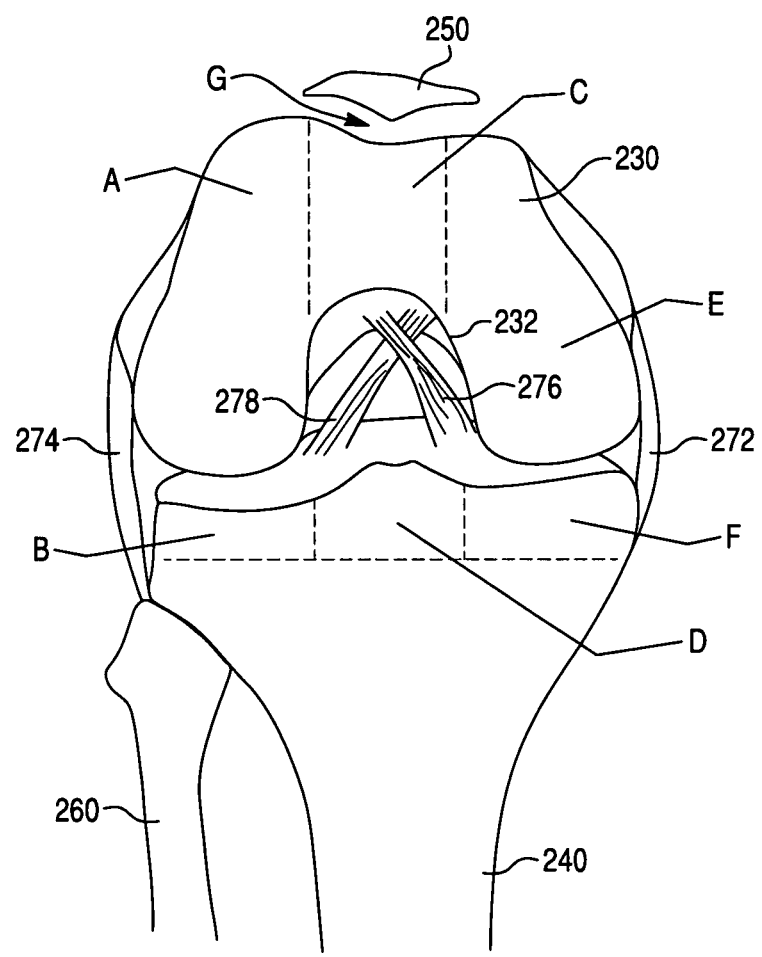

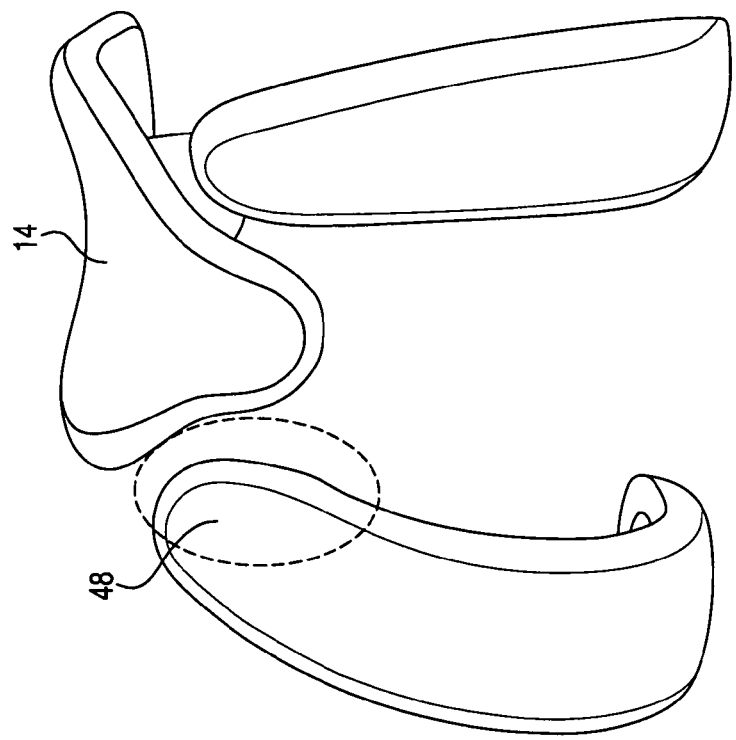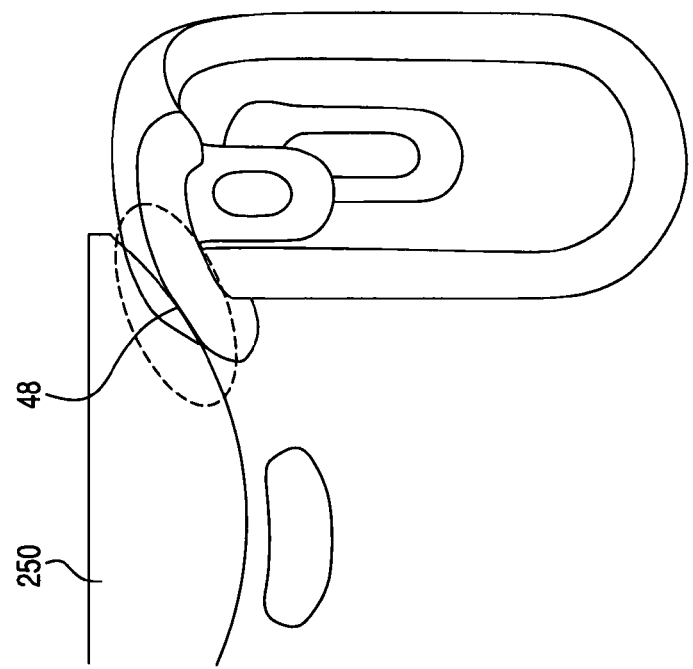

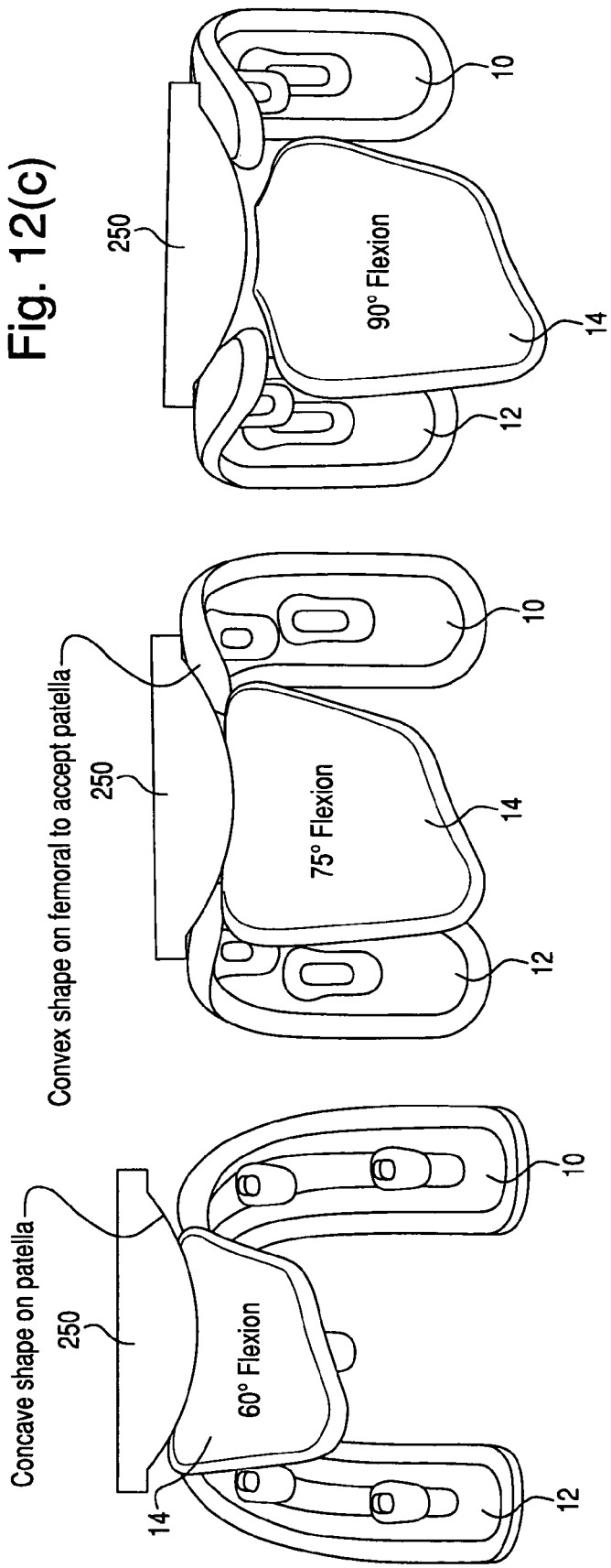

MULTI-COMPARTMENTAL PROSTHETIC DEVICE WITH PATELLAR COMPONENT TRANSITION

CROSS-REFERENCE TO RELATED PATENT APPLICATIONS

The present application claims priority to U.S. Provisional Application Nos. 61/068,053, filed Mar. 4, 2008; 61/068,059, filed Mar. 4, 2008; and 61/194,941, filed Oct. 2, 2008, each of which is hereby incorporated herein by reference in its entirety.

FIELD

The present invention relates to a prosthetic device configured to form at least a portion of a joint and, more particularly, to such a prosthetic device with a transition region extending from a patellofemoral component to a condyle component.

BACKGROUND

As shown in FIG. 1, conventional total knee arthroplasty (TKA) systems typically include a femoral component 500 that is implanted on the distal end of the femur and replaces the bearing surfaces of the femur, a tibial component 502 that is implanted on the proximal end of the tibia and replaces the bearing surfaces of the tibia and meniscus, and a patellar component (not shown) that replaces the articular surface of the patella. In such systems, the femoral component 500 is typically a single solid component. The tibial component 502 may include a tibial base plate (or tray) 502a that is affixed to the bone and a tibial insert 502b that is disposed on the tibial base plate 502a and forms the bearing surfaces of the tibial component 502. Alternatively, the tibial bearing surface may be cemented directly to the bone. In operation, the bearing surfaces of the femoral component 500 articulate against the bearing surfaces of the tibial component 502 as the knee joint moves through a range of motion.

One disadvantage of conventional TKA systems is that the incision must be large enough to accept implantation of the femoral component 500 and the tibial component 502. Another disadvantage is that the femoral component 500 and the tibial component 502 have standard, fixed geometries and are available in a limited range of sizes. As a result, the surgeon may be unable to achieve a fit that addresses each patient's unique anatomy, ligament stability, and kinematics. Additionally, because the conventional implant geometry is fixed, the surgeon may be forced to remove healthy as well as diseased bone to accommodate the implant. Thus, conventional TKA systems lack the flexibility to enable the surgeon to select implant components that are customized to accommodate a patient's unique anatomy and/or disease state.

In an effort to overcome disadvantages of conventional TKA systems, modular TKA knee prostheses comprising multiple components that are inserted separately and assembled within the surgical site have been developed. An example of a modular system is described in U.S. patent application Ser. No. 11/312,741, filed Dec. 30, 2005, published as U.S. Patent Application Publication 2006/0190086, and hereby incorporated by reference herein in its entirety. One disadvantage of such systems is that the modular components, although inserted separately, are connected together inside the patient's body. Thus, the modular components mimic a conventional TKA system, and, as a result, have limitations similar to those of a conventional TKA system. Additionally, because the modular components are fixed together, the components are dependent upon one another in that the selection and placement of one modular component is determined (or constrained) by the selection and placement of another modular component. For example, each modular component may include a connection mechanism (e.g., pins, screws, etc.) designed to mate with a corresponding connection mechanism on another modular component. Because the two components may mate together, the selection and placement of a component is determined and constrained by the selection and placement of the mating component. As a result, the degrees of freedom, interchangeability, and design variability of each modular component are restricted and the final geometry of the assembled component is fixed. Thus, conventional modular implants do not enable the surgeon to vary the placement or geometry of each modular component to best suit each patient's unique anatomy, ligament stability, kinematics, and disease state.

Furthermore, in a number of situations, knee replacement candidates have arthritis in only the medial and patellofemoral compartments, with an intact lateral compartment. If a monolithic component is used to replace only the medial and patellofemoral compartments of the femur and the medial compartment of the tibia (thus, leaving the lateral compartment and cruciate ligaments intact), the surgeon has fewer intra-operative options to best fit the implant to the patient's anatomy.

Efforts have been made to develop multi-compartmental, non-connected systems that do not suffer shortcomings, such as those mentioned above. Such systems can include, for example, non-connected patellofemoral and femoral condyle components. However, with such multi-compartmental, non-connected systems there is a potential that there will not be a smooth transition of the patella or patellar component from the patellofemoral component to the femoral condyle component(s). This can result, for example, in shortened life of the patella or patellar implant or even failure. In addition, it may cause discomfort to the patient.

SUMMARY OF THE INVENTION

According to one embodiment of the present invention, a prosthetic device configured to form at least a portion of a joint may comprise a plurality of segmented components configured to be fixed relative to a femur of a body including: a patellofemoral component and a condyle component. Each segmented component may be configured such that a placement at which the segmented component will be fixed relative to the femur is not constrained by a connection to another of the segmented components that is fixed relative to the femur. In an installed configuration, the patellofemoral and condyle components are configured to be fixed relative to the femur such that: a gap is provided between an edge of the patellofemoral component and an opposing edge of the condyle component, wherein the gap includes a portion having a substantially uniform width with a midline that is substantially parallel to a trochlear groove of the patellofemoral component, and a transition region is provided that extends from a first femoral coronal plane that intersects the patellofemoral component to a second femoral coronal plane that intersects the condyle component. The transition region may include a divergence point at which an articular surface of the patellofemoral component diverges superiorly away from an articular surface of the condyle component.

It is to be understood that both the foregoing general description and the following detailed description are exemplary and explanatory only, and are not restrictive of the invention as claimed.

BRIEF DESCRIPTION OF THE DRAWINGS

The features, aspects, and advantages of the present invention will become apparent from the following description, appended claims, and the accompanying exemplary embodiments shown in the drawings, which are briefly described below.

FIG. 2 is a coronal view of a knee joint.

FIG. 11(a) is a cross sectional view of a patella transition with small regions of concavity according to an embodiment of the present invention.

FIG. 11(b) is a perspective view of the patella transition of FIG. 11(a).

FIG. 12(a) is a top view of a patella transition according to another embodiment of the present invention in which the patella contacts only a patellofemoral component of the prosthetic device.

FIG. 12(b) is a top view of the patella transition of FIG. 12(a) in which the patella contacts both the patellofemoral component and condyle components.

FIG. 12(c) is a top view of the patella transition of FIG. 12(a) in which the patella contacts only the condyle components.

DETAILED DESCRIPTION

Figure 1:
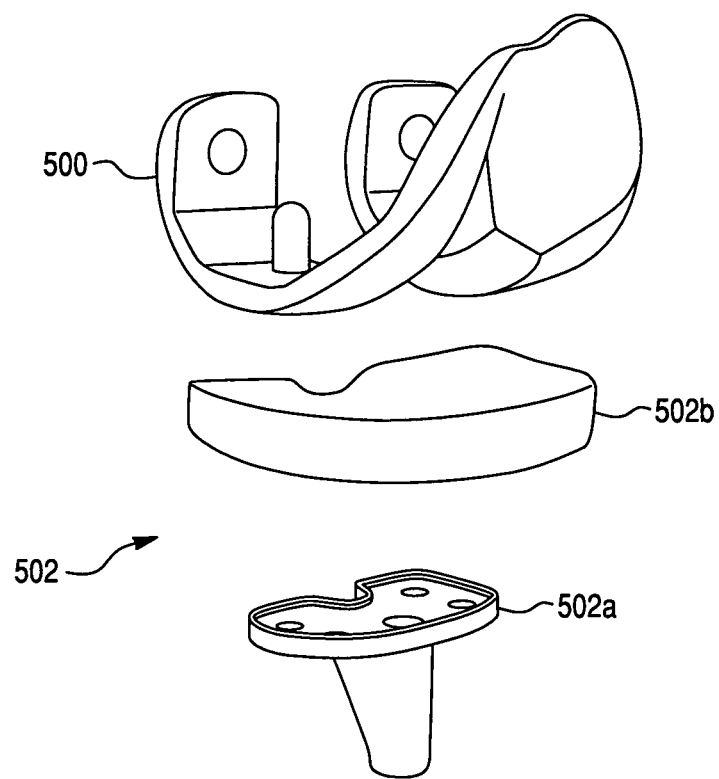
FIG. 1 is a perspective view of a conventional total knee arthroplasty system.

The following discloses embodiments of the present invention that provide techniques and implants that can be configured to enable individual components of a prosthetic device to be selected and implanted in one, two, or three compartments of a joint with a high degree of accuracy and in any combination that enables the surgeon to vary the geometry and configuration of the implant to create a customized prosthetic device tailored to the patient's unique anatomy, ligament stability, kinematics, and disease state. Moreover, the implant components can be configured to provide a smooth transition of the patella or patellar implant from component to component. Preferred embodiments are illustrated in the drawings. An effort has been made to use the same or like reference numbers throughout the drawings to refer to the same or like parts.

FIG. 2 is a diagram of a knee joint that includes a distal end of a femur 230, a proximal end of a tibia 240, a fibula 260, and a patella 250. The patella 250 moves relative to the femur 230 and the tibia 240 when the knee joint articulates. The femur 230 is joined to the tibia 240 by a medial collateral ligament (MCL) 272, a posterior cruciate ligament (PCL) 278, and an anterior cruciate ligament (ACL) 276. The femur 230 is joined to the fibula 260 by a lateral collateral ligament (LCL) 274.

The distal end of the femur 230 can be conceptually divided into a lateral (i.e., outside) condyle region A, a central (or patellofemoral) region C (which contains a patellar groove 232 having an inverted U-shape), and a medial (i.e., inside) condyle region E. Similarly, the proximal end of the tibia 240 can be conceptually divided into lateral B, central D, and medial F regions, which correspond, respectively, to the lateral A, central C, and medial E regions of the femur 230. Finally, the space between the patella 250 and the femur 230 or the tibia 240 (depending on the bending state of the leg) defines a patellar region G.

FIGS. 3(a), 3(b), 3(c), and 3(d) show embodiments of a prosthetic device 5 according to the present invention. In this embodiment, the prosthetic device 5 is a knee implant. The present invention, however, is not limited to this particular configuration. The prosthetic device 5 may be any orthopedic joint implant, such as, for example, a bicompartmental (FIG. 3(c)) or tricompartmental (FIGS. 3(a), 3(b), and 3(d)) knee implant. In the alternative the prosthetic device may be a trial of an implant.

Figure 3A:
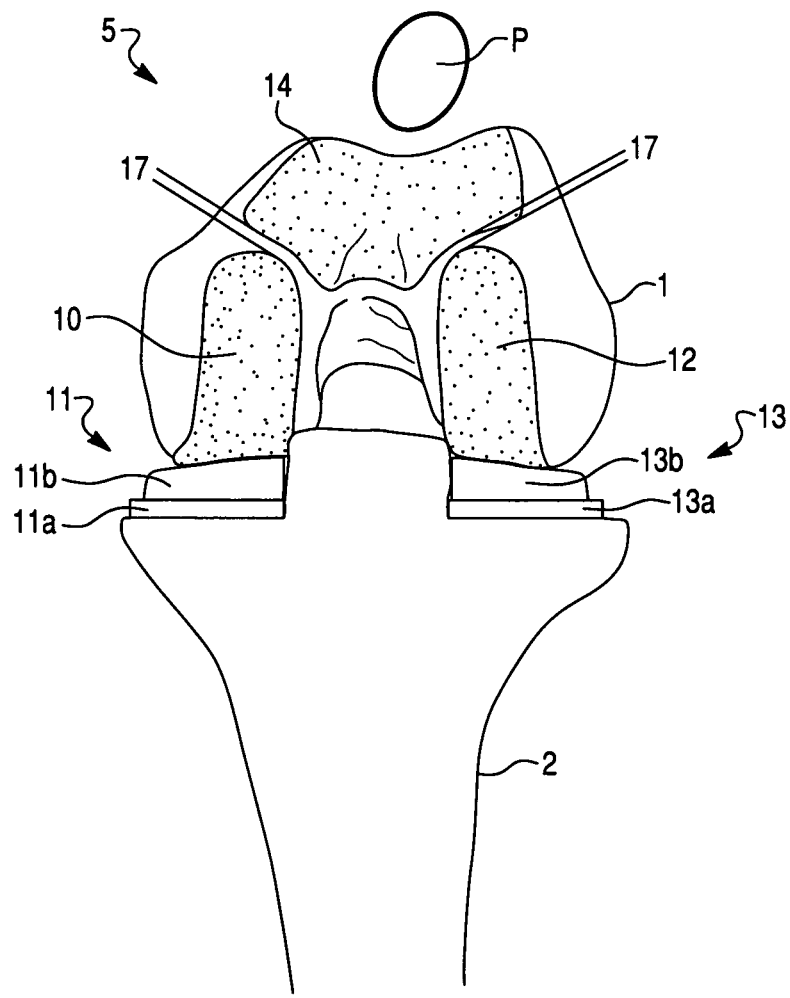
FIG. 3(a) is a perspective view of a prosthetic device implanted in a knee joint according to an embodiment of the present invention.
Figure 3B:
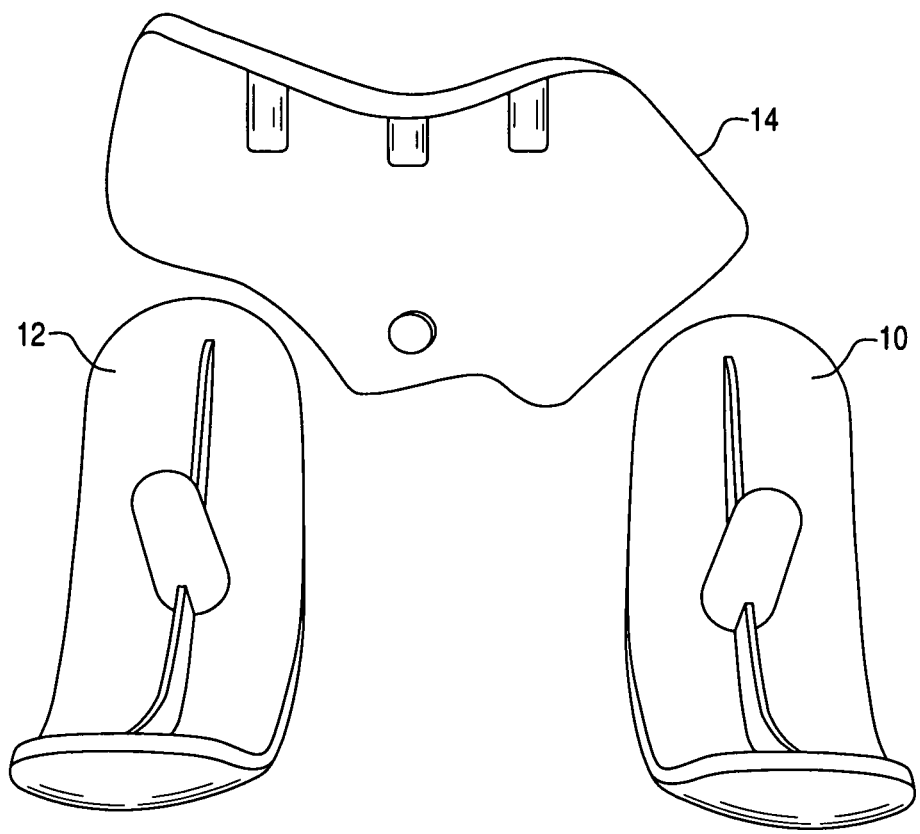
FIG. 3(b) is a perspective view of an underside of the femoral components of the prosthetic device of FIG. 3(a).
Figure 3C:
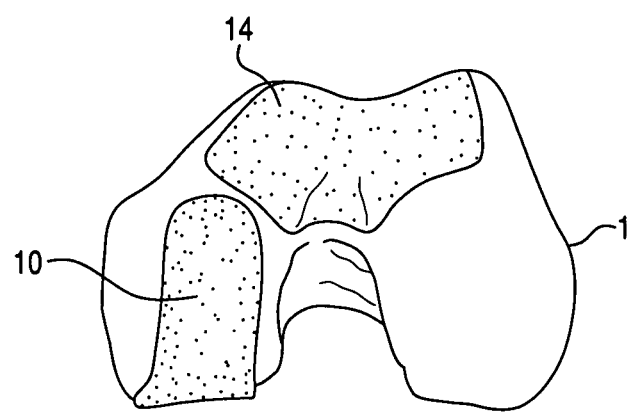
FIG. 3(c) is a perspective view of the femoral components of the prosthetic device of FIG. 3(a) in a bicompartmental (medial and patellofemoral) configuration according to an embodiment of the present invention.
Figure 3D:
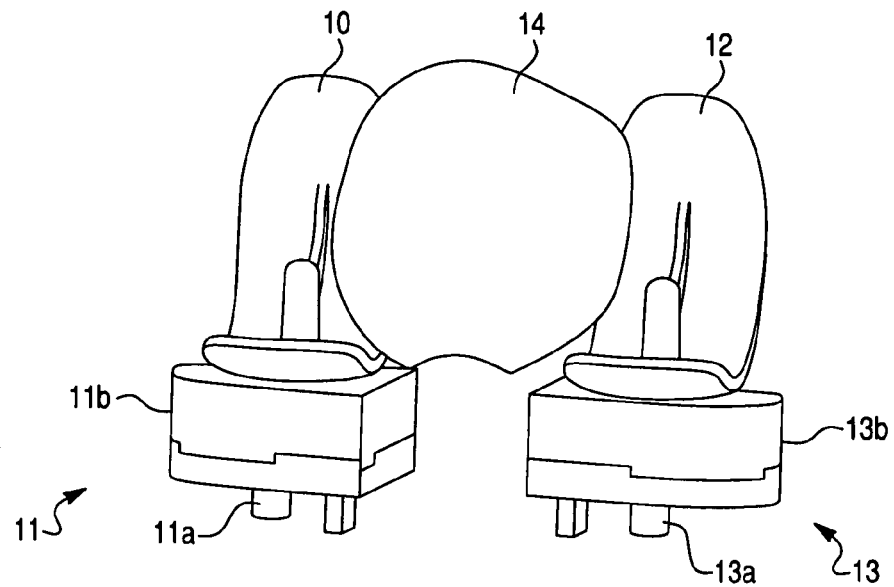
FIG. 3(d) is a perspective view of a prosthetic device according to another embodiment of the present invention.
Figure 4:
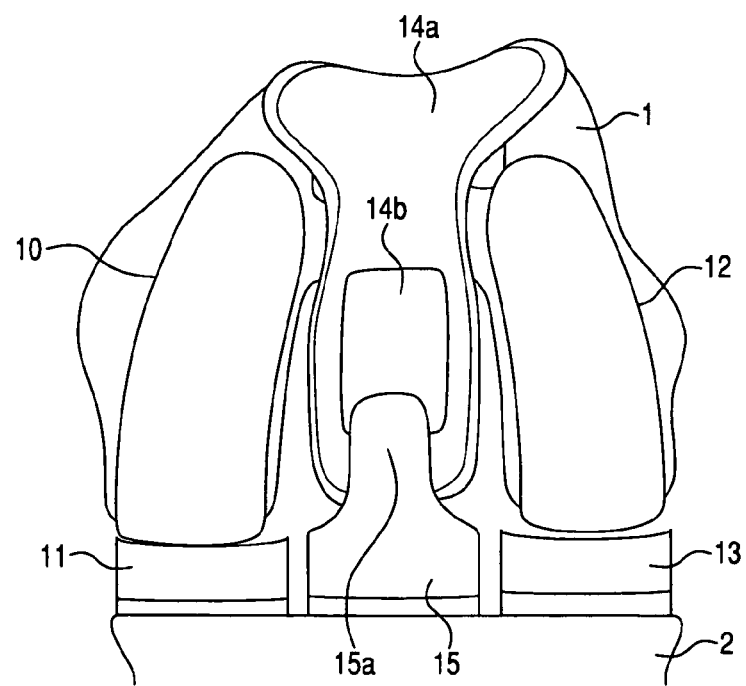
FIG. 4 is a perspective view of a prosthetic device implanted in a knee joint according to an embodiment of the present invention.

The prosthetic device 5 can include a plurality of components configured to be implanted in a body of a patient to form at least a portion of a joint, such as a knee joint as shown in FIG. 3(a). In this embodiment, the prosthetic device 5 includes a first component 10, a second component 12, and a third component 14 each configured to be fixed relative to a first bone 1 of the body. The prosthetic device 5 also may include a fourth component 11 and a fifth component 13 each configured to be fixed relative to a second bone 2 of the body. The prosthetic device 5 may also include additional components, such as a sixth component 15 configured to be fixed relative to the second bone 2, as shown in FIG. 4. In the embodiment of FIG. 4, the third component 14 is replaced with a third component 14a that includes a recess 14b adapted to engage a projection 15a of the sixth component 15 to provide posterior stabilization, as described, for example, in U.S. patent application Ser. No. 11/684,514, filed Mar. 9, 2007, published as U.S. Patent Application Publication 2008/0058945, and hereby incorporated by reference herein in its entirety. In these embodiments, the components 10, 12, 14, and 14a comprise femoral components, and the first bone 1 is a femur. The components 11, 13, and 15 comprise tibial components, and the second bone 2 is a tibia. However components on a second bone, e.g., the tibia, are not necessary for the invention The components of the prosthetic device 5 are preferably segmented components. As shown in FIGS. 3(a) and 3(b), a segmented component is an individual component implanted in the joint as an independent, self-contained, stand-alone component that is not physically constrained by any other segmented component (as used herein, the term physically constrained means that the components are linked through a physical connection and/or physical contact in such a manner that the link between the components imposes limitations on the positioning or placement of either of the components). Thus, the components 10, 11, 12, 13, and 14 are all segmented components. Although a segmented component is an independent, stand-alone component, a segmented component itself may be formed by joining multiple components together (e.g., via mechanical joint, bonding, molding, etc.). For example, the segmented component 11 may be a medial tibial component formed by connecting a modular tibial base plate 11*a* and a modular tibial insert 11*b* to form the independent, stand-alone medial tibial component 11. Although formed from multiple pieces, the tibial component 11 is a segmented component according to the present invention because, when implanted in the joint, it is not physically constrained by any other segmented component of the prosthetic device 5, such as the component 13 (shown in FIG. 3(*a*)) or the component 15 (shown in FIG. 4). In another example, a segmented component may have lugs or pegs (such as projections 80 in FIG. 8) that are modular and attach to the component. To ensure that a segmented component is not physically constrained by other components, the segmented component may be implanted in the joint so that the component is not connected to and/or in contact with any other segmented component. For example, in one embodiment, the components of the prosthetic device 5 are configured such that the components can be implanted to form the prosthetic device 5 without being connected, as shown in FIGS. 3(*a*) and 4. In this embodiment, the components 10, 12, and 14 are not interconnected when fixed relative to the first bone 1. Similarly, the components 11, 13, and 15 are not interconnected when fixed relative to the second bone 2. In another embodiment, the components of the prosthetic device 5 are configured such that the components can be implanted to form the prosthetic device 5 without being in contact, as shown in FIGS. 3(*a*) and 4. In this embodiment, the components 10, 12, and 14 are physically separated from one another when fixed relative to the first bone 1. For example, as shown in FIG. 3(*a*), the components 10 and 12 are each separated from the component 14 by a gap 17. Similarly, the components 11, 13, and 15 are physically separated from one another when fixed relative to the second bone 2.

One advantage of a prosthetic device having unconnected and/or physically separated components is that the surgeon does not have to consider whether a particular component is designed to mate with other components of the prosthetic device 5. Instead, the surgeon can select each component based on how that particular component will fit to the specific patient anatomy and the expected performance in the specific region of the joint in which it will be implanted. As a result, the surgeon can create a customized prosthetic device, for example, by selecting each component to have the performance characteristics (e.g., size, geometry, conformity, orientation, angle, etc.) best suited for the particular portion of the joint in which it will be installed. In contrast, with conventional modular implants, the surgeon may use modular components that have corresponding connection mechanisms. Thus, the surgeon may be limited to the implant manufacturer's predetermined component combinations and/or forced to select components having less desirable performance characteristics just to ensure that the components can be successfully mated together.

Another advantage of a prosthetic device having unconnected and/or physically separated components is that the position of each component on the bone is not constrained or hindered by the position of any other component on the bone. Thus, a pose (i.e., position and orientation) or placement at which each component is fixed relative to the bone is not constrained by a connection to or contact with another component. As a result, the degrees of freedom available when positioning a component are not limited or restricted by any other component. As a result, the surgeon has freedom to customize the placement (e.g., alignment, orientation, rotation, translation, etc.) of each component of the prosthetic device to meet the specific needs of the patient (e.g., based on unique anatomy, ligament stability, kinematics, and/or disease state). In contrast, conventional TKA implants include monolithic components having fixed geometry. Similarly, conventional modular implants include modular pieces that are fixed together after insertion into the body resulting in fixed geometry. Because the geometry is fixed, the surgeon does not have the freedom to independently position each modular piece.

Another advantage of a prosthetic device having unconnected and/or physically separated components is that the configuration of the prosthetic device 5 is variable. For example, because the components do not constrain one another, the combinations of components forming the prosthetic device 5 can be varied (e.g., mixed and matched) to include any number, type, and/or combination of components appropriate for a particular patient. The appropriate number, type, and/or combination of components may be determined based on patient specific factors such as, for example, the patient's unique anatomy, ligament stability, kinematics, and/or disease state. Thus, by varying the number, type, and/or combination of components, the surgeon can customize the prosthetic device 5 to target osteoarthritic disease by joint compartment. In contrast, with conventional TKA systems, there are typically up to eight different implant sizes offered for each component, and the average size increment is between 3-5 mm. These implants may have a fixed ratio between the anterior-posterior and the medial-lateral dimensions with other implant geometry being accordingly constrained. Because each patient's bone generally does not perfectly match the TKA implant size offering, the surgeon may compromise by downsizing or upsizing the component. Additionally, conventional TKA designs require the removal of a significant amount of bone to eliminate variations in the patient's joint geometry and ensure that one of the available implants will fit. As a result, ligament balance could be slightly looser or tighter than desired, or certain compartments could be overstuffed (i.e., more metal or plastic added than bone removed). In addition, the generally symmetric condyles of the femoral TKA component and the generally symmetric condyles of the tibial TKA component may not perfectly fit the patient's natural asymmetric anatomy. Another problem is that the kinematics of the joint following a TKA procedure are typically different from the natural kinematics. Thus, although the patient experiences significant improvement (e.g., reduced pain, increased range of motion, etc.), full function of the joint is not restored. In contrast, the present invention advantageously provides a segmented implant system with components having multiple sizes, shapes, geometries, and conformities to enable construction of a prosthetic device 5 customized to a particular patient's unique anatomy, ligament stability, kinematics, and/or disease state.

In operation, to target a patient's unique disease state, the surgeon can configure the prosthetic device 5 to address disease in any compartment of the joint. Specifically, the surgeon can mix and match the components of the prosthetic device 5 to provide the desired coverage. For example, the prosthetic device 5 may include components configured for implantation on a first compartment of a knee joint (e.g., a medial compartment), components configured for implantation on a second compartment of the knee joint (e.g., a lateral compartment), and/or components configured for implantation on a third compartment of the knee joint (e.g., a central or patellofemoral compartment). As a result, the prosthetic device 5 can be configured as a bicompartmental or tricompartmental implant. Thus, the surgeon can vary an arrangement of the components to form a prosthetic device customized to the patient's unique anatomy, disease state, ligament stability, and kinematics.

In one embodiment, the components of the prosthetic device 5 are configured to form a tricompartmental implant. In this embodiment, the prosthetic device 5 includes at least three segmented components each configured to be fixed relative to a corresponding bone of the joint. The tricompartmental implant may be cruciate retaining (shown in FIG. 3(*a*)) for patients whose posterior cruciate ligament (PCL) and anterior cruciate ligament (ACL) are healthy and intact or posterior stabilized (shown in FIG. 4) for patients whose PCL is damaged and/or may be excised. In the cruciate retaining embodiment of FIG. 3(*a*), the components 10, 12, and 14 form a femoral portion of the tricompartmental implant. Components 11 and 13 can be used to form a tibial portion of the tricompartmental implant, but they are not required. For the femoral portion, the component 10 may be a medial femoral component configured to be fixed relative to the medial femoral region E of the first bone 1, the component 12 may be a lateral femoral component configured to be fixed relative to the lateral femoral region A of the first bone 1, and the component 14 may be a patellofemoral component configured to be fixed relative to the central femoral region C of the first bone 1. For the tibial portion, the component 11 may be a medial tibial component (e.g., including a base plate 11*a* and an insert 11*b*) configured to be fixed relative to the medial tibial region F of the second bone 2, and the and the component 13 may be a lateral tibial component (e.g., including a base plate 13*a* and an insert 13*b*) configured to be fixed relative to the lateral tibial region B of the second bone 2. The prosthetic device 5 may also include a patella or patellar component P (hereinafter referred to collectively as a patellar component).

Figure 5:
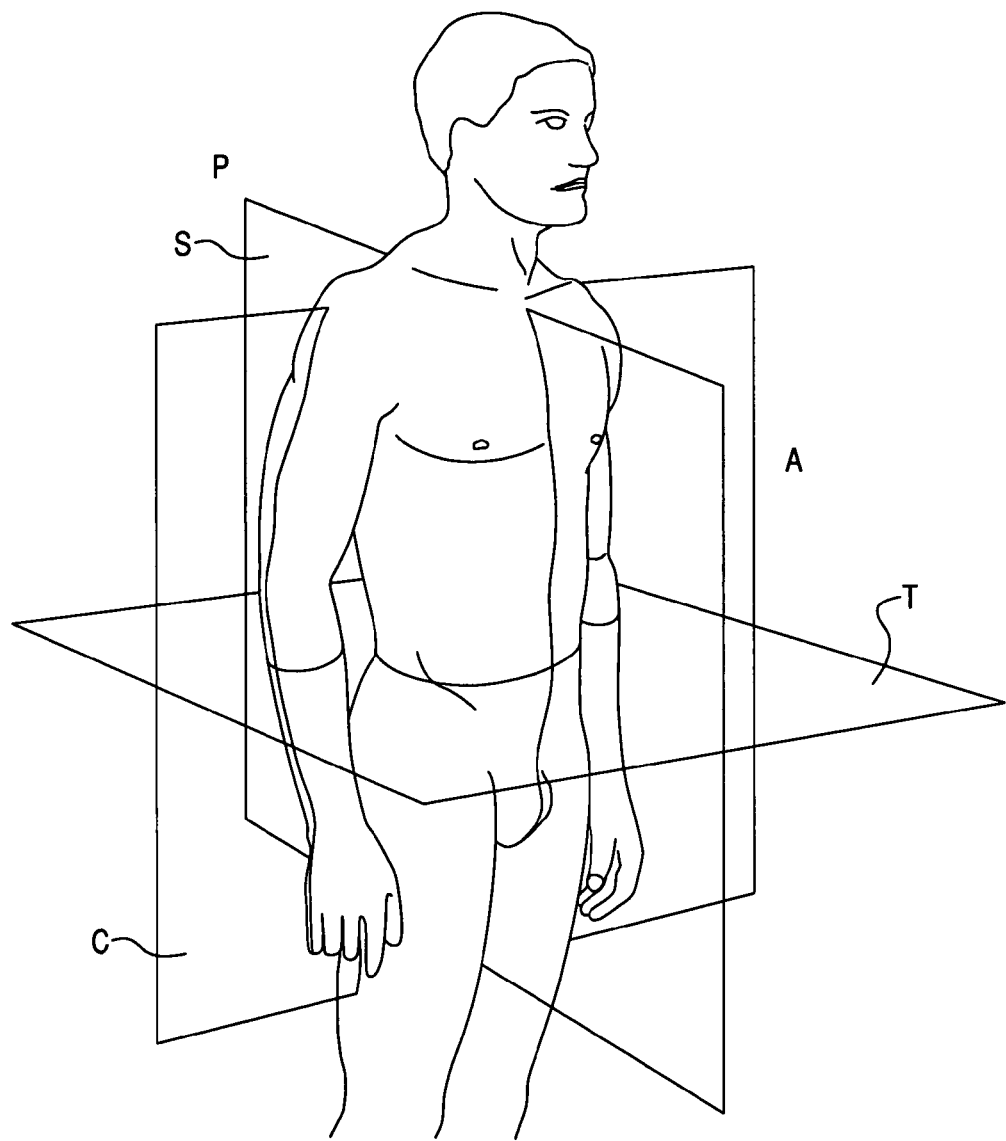
FIG. 5 is an illustration of the sagittal, transverse, and coronal anatomical planes.
Figure 6:
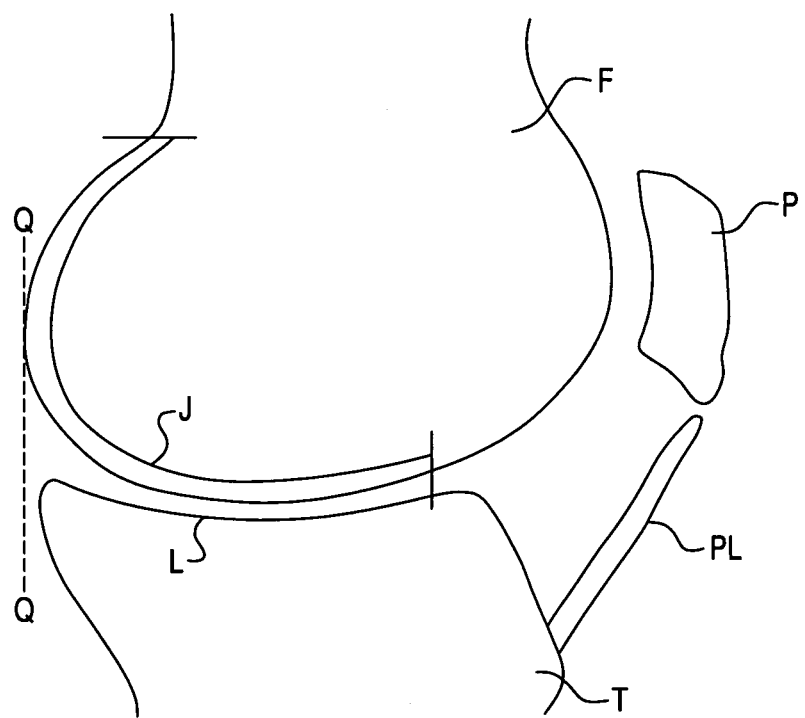
FIG. 6 is a cross-sectional sagittal view of a femur and a tibia of a knee joint.

To aid in the description of the following embodiments of the present invention, reference can be made to FIGS. 5-6. FIG. 5 shows anatomical planes of the body including a sagittal plane S, a transverse plane T, and a coronal plane C. The front of the body is known as anterior (A), and the back of the body is known as posterior (P). Thus, the sagittal plane S is an anterior-posterior (AP) plane. In a knee joint, the medial condyle of the femur F has a different sagittal geometry than the lateral condyle of the femur F. The sagittal shape of the femur F is commonly known as the j-curve because it is made of several arcs of varying radii, larger distally and smaller posteriorly, whose silhouette resembles the shape of a "J" as shown in FIG. 6. The radii of the medial and lateral arcs are different, and the angle at which the radii transition from one arc to the next also varies. Similarly, the sagittal cross-sectional shape of the medial tibial plateau is different from the sagittal cross-sectional shape of the lateral tibial plateau. The medial tibial side is generally described as more concave (or cup shaped or conforming). Conversely, the lateral tibial side is commonly described as convex (or flat or non-conforming). These shape differences between the medial and lateral sides of the femur F and the tibia T affect the net normal force of the contact region. For example, when contact vectors between the medial and lateral sides are not parallel, a moment develops between compartments, including an axial rotation moment that imparts axial rotation between the femur F and the tibia T. Additionally, these differences in shape of the articular surfaces of the tibia enable kinematics of the joint throughout the range of motion, including rotation, translation of the bones, and internal rotation that occurs during the gait cycle.

In a natural joint, the sagittal shape of the medial tibial plateau has a low point or sulcus L located at approximately a midpoint of the plateau in an anterior-posterior (front-back) direction. At full extension, the femur F rests in the sulcus L as shown in FIG. 6. When viewed in the sagittal plane S, the posterior femoral condyle is nearly flush with the posterior tibia T as indicated by a line Q-Q in FIG. 6. At this position, the anterior femur F is more anterior than the tibia T. As a result a patellar ligament PL is directed anteriorly. During flexion, a force develops in the patellar ligament PL due to quadriceps activation and causes the tibia T to translate anteriorly or the femur F to translate posteriorly. This is known as femoral rollback.

Figure 7:
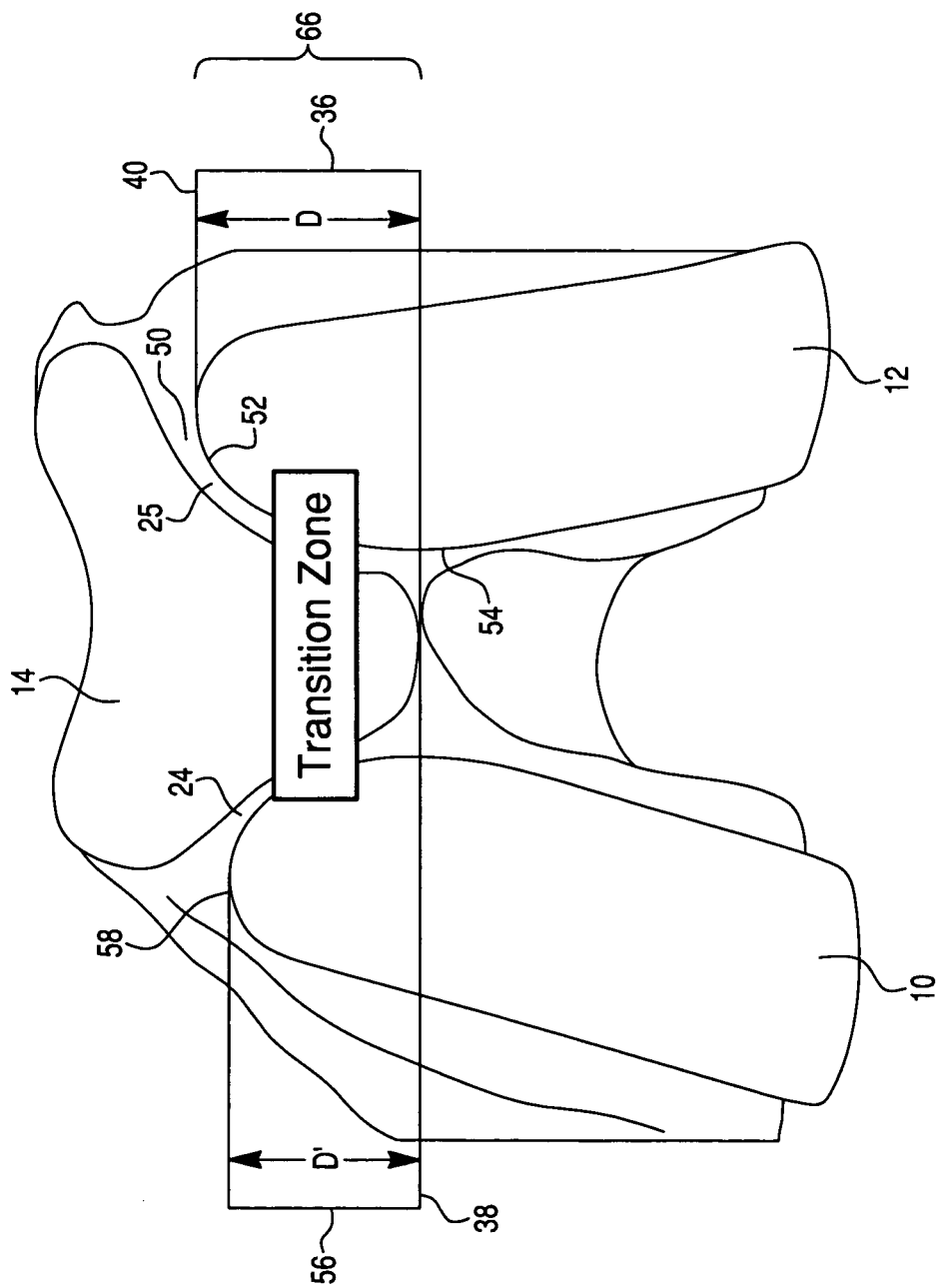
FIG. 7 is a distal view of a patella transition of a prosthetic device in an installed configuration according to another embodiment of the present invention.
Figure 8:
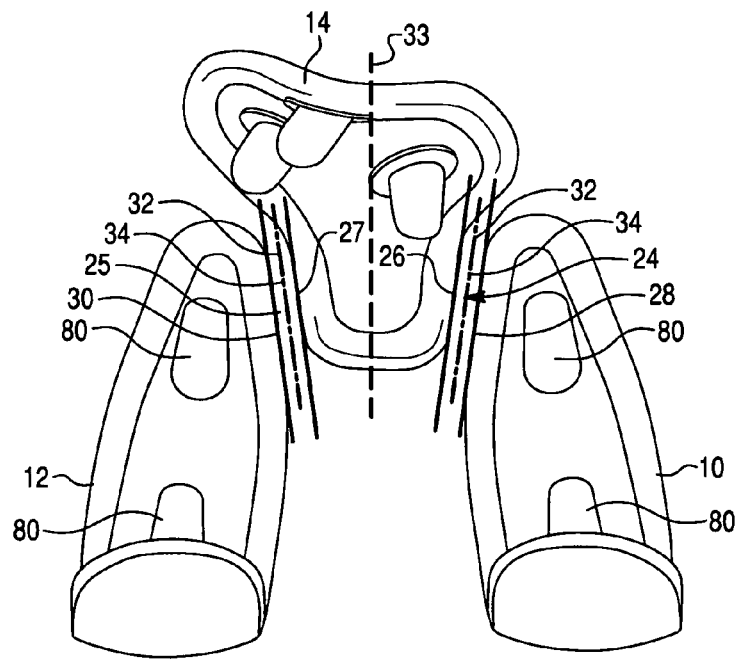
FIG. 8 is a top view of the patella transition of FIG. 7.

FIGS. 7-8 show a preferred embodiment of the present invention. With this embodiment (which can be either bicompartmental or tricompartmental), the patellofemoral and femoral condyle or components are split apart and nested together without touching. Because the components are separate, they can be positioned relative to each other to best match the patient's anatomy. Because the compartmental components do not have to be physically touching or united together, both the femoral condyle component(s) and patellofemoral component can be positioned independent of each other within a small positioning envelope. However, this preferred embodiment can be configured to provide the advantage of having a prosthetic device with a smooth patella transition from the patellofemoral component to the femoral condyle component (if the prosthetic device is bicompartmental) or to both femoral condyle components (if the prosthetic device is tricompartmental), which may, for example, increase patella component life, prevent failure, and/or avoid discomfort to the patient.

As an overview of the embodiment of FIGS. 7-8, the patellar component (not shown in FIGS. 7-8) can be handed-off between the femoral components in a 3-stage process in order to facilitate a smooth patella transition. From extension to flexion, in a first stage, the patellar component initially contacts only the patellofemoral component 14. Then, in a second stage, the patellar component initiates contact with the femoral condyle component(s) 10, 12 while simultaneously contacting the patellofemoral component 14. Finally, in a third stage, the patellar component only contacts the femoral condyle component(s) 10, 12. This 3-stage process can be used for patellar components with differing configurations, such as substantially Gaussian-shaped (called "sombrero"), dome or semispherical-shaped, and conical or v-shaped type patellar components.

In the embodiment shown in FIGS. 7-8, the prosthetic device 5 is configured to form at least a portion of a joint. The prosthetic device 5 may comprise a plurality of segmented components configured to be fixed relative to the femur of the body. The plurality of segmented components may include the component 14 and at least one or both of the component 10 and the component 12. The components 10 and 12 may be condyle components in which the component 10 may be a medial femoral component configured to be fixed relative to the medial femoral region E of the first bone 1 and the second component 12 may be a lateral femoral component configured to be fixed relative to the lateral femoral region A of the first bone 1. The component 14 may be a patellofemoral component configured to be fixed relative to the central femoral region C of the first bone 1. Each segmented component is configured such that a placement at which the segmented component will be fixed relative to the femur is not constrained by a connection to another of the segmented components that is fixed relative to the femur.

In an installed configuration (e.g., a configuration in which the components are implanted on the bone as shown in FIG. 7), the patellofemoral component 14 and the one or more femoral condyle components 10 and 12 are configured to be fixed relative to the femur such that a gap 24 is provided between an edge 26 of the patellofemoral component 14 and an opposing edge 28 of the condyle component 10 and/or a gap 25 is provided between an edge 27 of the patellofemoral component 14 and an opposing edge 30 of the condyle component 12. The gaps 24 and 25 are best illustrated in FIG. 8, which shows a top view of the implant components in the installed configuration with the image of the bone removed. The geometry of the gaps 24 and 25 is advantageously configured to enable a smooth patella transition while providing tolerance for some misalignment between the implant components.

For example, the gaps 24 and 25 may each include a portion 34 having a substantially uniform width with a midline 32 that is substantially parallel or at an angle to a trochlear groove 33 of the patellofemoral component 14. For example, the midline 32 may extend at an angle less than about 45 degrees relative to the trochlear groove 33 of the patellofemoral component 14. In a preferred embodiment, the midline 32 extends at an angle of less than about 20 degrees relative to the trochlear groove 33. In another embodiment, the midline 32 extends at an angle of less than about 5 degrees relative to the trochlear groove 33. Generally, after about 30 degrees of flexion, the patellar component is fully constrained by the patellofemoral component 14 such that the patellar component tracks along the trochlear groove 33 when the patellar component is in contact with the patellofemoral component 14. Thus, in the region where the patellar component follows the trochlear groove 33, the midline 32 is substantially parallel or at an angle to the patellar component tracking pathway.

Figure 13:
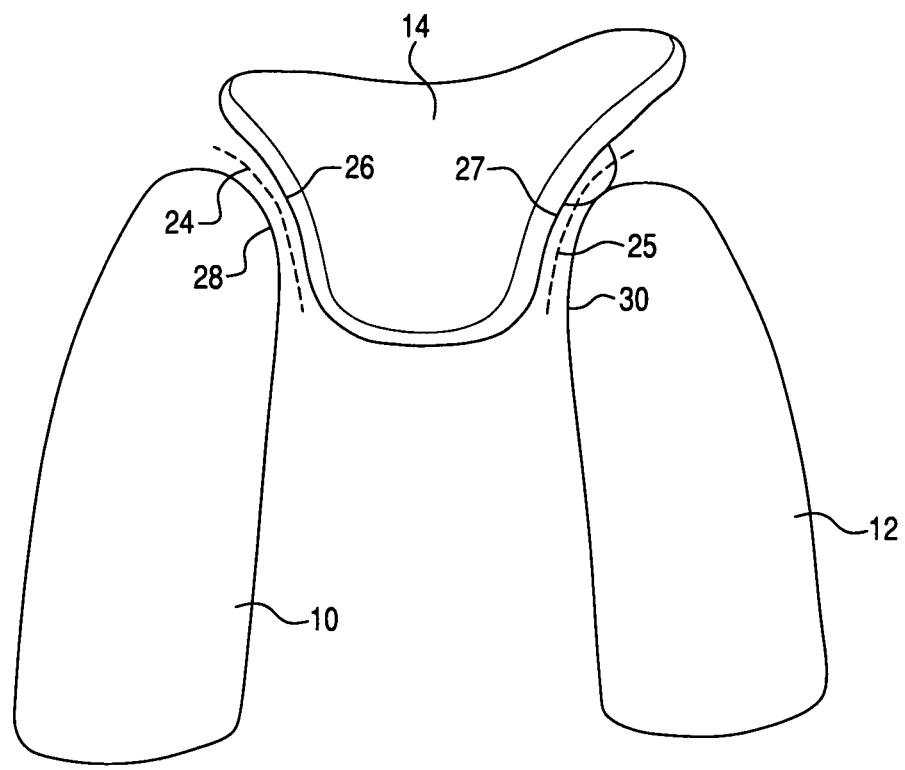
FIG. 13 is a distal view of a patella transition according to an embodiment of the present invention.

The substantially uniform width of the portion 34 of each gap 24, 25 can be configured in a variety of ways, some of which are described here. For example, according to one embodiment, the edges creating the substantially uniform portion 34 of the gap 24 and/or the gap 25 may be substantially straight lines that are substantially parallel. For example, as shown in FIG. 8, the edges 26 and 28 are substantially straight and substantially parallel to one another. Similarly, the edges 27 and 30 are substantially straight and substantially parallel to one another. According to another embodiment, the edges creating the substantially uniform portion 34 of the gap 24 and/or the gap 25 may be substantially concentric arcs. For example, as shown in FIG. 13, the edges 26 and 28 may be concentric arcs. Similarly, the edges 27 and 30 may be concentric arcs. In a preferred embodiment, the arcs of the edges 28, 30 of the femoral condyle components 10, 12 each have a radius greater than 20 mm. In another preferred embodiment, that radius is preferably greater than 15 mm. In both instances, the arcs of the edges 26, 27 of the patellofemoral component 14 preferably each have a radius greater than or equal to the sum of the arc of the respective edge 26, 27 plus the respective gap 24, 25. In this embodiment, although the midline of the gap 24 and/or the gap 25 is slightly curved, the edges are oriented such that one or more portions of the midline are substantially parallel or at an angle to a trochlear groove 33 of the patellofemoral component 14.

According to another embodiment, an edge of the patellofemoral component and an opposing edge of a condyle component may diverge, yet still provide a substantially uniform width. For example, the edge 26, 27 of the patellofemoral component 14 may be substantially straight while a corresponding edge 28, 30 of femoral condyle component 10, 12 may be an arc. As another example, the edge 26, 27 of the patellofemoral component 14 may be an arc while a corresponding edge 28, 30 of femoral condyle component 10, 12 may be substantially straight. In such cases, the edge 26, 27 of the patellofemoral component 14 and the corresponding edge 28, 30 of the femoral condyle component 10, 12 preferably diverge less than about 20 degrees to provide the substantially uniform width of the gap 24, 25. According to other embodiments, that divergence angle may be greater or smaller so as to provide the substantially uniform width. For example, the divergence angle may be less than about 30 degrees or may be less than about 10 degrees.

In each of the embodiments, the uniform widths of the portions 34 of the gaps 24 and 25 may be the same or different. Moreover, their degree of uniformity may be the same or different. According to a preferred embodiment, the width of the gap 24 and the width of the gap 25 may be less than about 4 mm. In addition, in one embodiment, edge fillets for all components are greater than 1.5 mm, preferably from 2 to 3 mm. According to a preferred embodiment, the edges creating the substantially uniform portion 34 of the gaps 24 and 25 may be substantially straight and parallel to the trochlear groove 33 of the patellofemoral component 14 or the patellar component tracking pathway in the region of potential patellar component contact. In one embodiment, the gaps 24 and 25 in the region of potential patellar component contact are each substantially straight having an arc larger than 20 mm on the medial side, the edges of the implant components that form the gaps are either parallel or concentric with each other, and the gaps are substantially parallel (e.g., 5 degrees or less) to the trochlear groove 33 or the patellar component tracking pathway.

The patellofemoral component 14 and the femoral condyle component 12 are configured to be fixed relative to the femur such that a transition region 36 is provided that extends from a first femoral coronal plane 38 that intersects the patellofemoral component 14 to a second femoral coronal plane 40 that intersects the condyle component 12. As shown in FIG. 7, the transition region 36 may extend from a location where the first femoral coronal plane 38 intersects the most posterior portion of the patellofemoral component 14 to a location where the second femoral coronal plane 40 intersects the most anterior portion of the condyle component 12. Thus, in the installed configuration, the components overlap such that the anterior tip of the condyle component 12 is disposed more anteriorly than the posterior tip of the patellofemoral component 14. According to one embodiment, a distance D between the first and second femoral coronal planes is greater than about 5 mm to enable sufficient time and surface area for a smooth patella transition during flexion. In one embodiment, the distance D is approximately 5-12 mm. Preferably, there should be substantial overlap of the patellofemoral component 14 and the femoral condyle component 12, such as a distance D of preferably 10 mm or more.

Figure 10C:
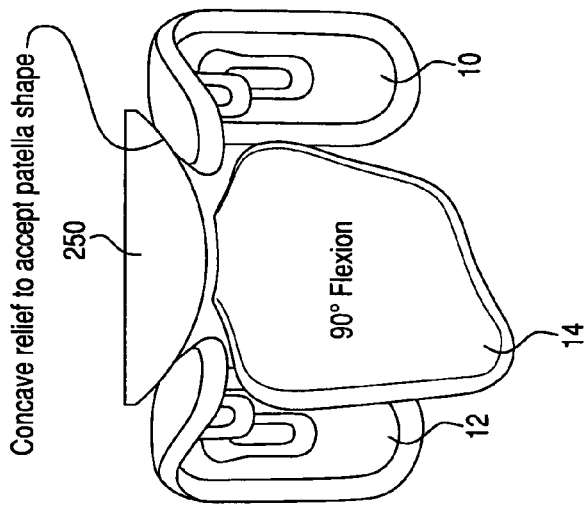
FIG. 10(c) is a top view of the patella transition according to the embodiment of FIG. 9 in which the patella contacts only the condyle components.
Figure 10B:
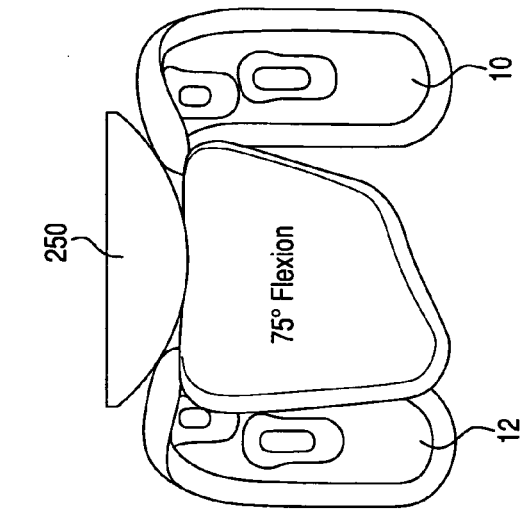
FIG. 10(b) is a top view of the patella transition according to the embodiment of FIG. 9 in which the patella contacts both the patellofemoral component and condyle components.
Figure 10A:
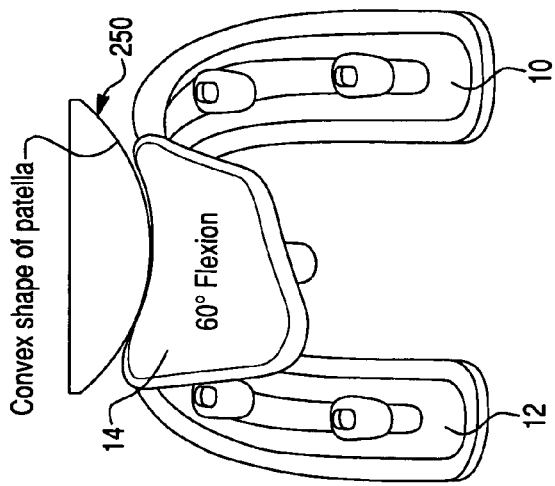
FIG. 10(a) is a top view of the patella transition according to the embodiment of FIG. 9 in which the patella contacts only a patellofemoral component of the prosthetic device.

Similarly, in an installed configuration, a second transition region 56 can extend from the first femoral coronal plane 38 to a third femoral coronal plane 58 that intersects the second condyle component 10. For example, the third femoral coronal plane 58 may intersect the most anterior portion of the second condyle component 10. Thus, in the installed configuration, the components overlap such that the anterior tip of the condyle component 10 is disposed more anteriorly than the posterior tip of the patellofemoral component 14. According to one embodiment, a distance D' between the first and third femoral coronal planes is greater than about 5 mm to enable sufficient time and surface area for a smooth patella transition during flexion. In one embodiment, the distance D' is approximately 5-12 mm. Preferably, there should be substantial overlap of the patellofemoral component 14 and the femoral condyle component 10, such as a distance D' of preferably 10 mm or more. In the embodiment of FIG. 7, the distance D' is less than the distance D. Of course, the distances D and D' can be substantially the same or different. The transition regions 36 and 56 (collectively, a transition region 66) are configured to provide adequate time and surface area for the patellar component to transition from the patellofemoral component to the condyle components as the patient moves the joint from extension to flexion. Optimal transition smoothness is achieved by configuring the prosthetic device so that the patellar component transitions within the transition region 66. According to one embodiment, the patellar component transitions as described in the aforementioned 3-stage transition process, which is illustrated in FIGS. 10(a)-10(c). In this embodiment, the transition region 66 includes at least a first portion 50 (e.g., corresponding to a flexion angle of about 60 degrees), a second portion 52 (e.g., corresponding to a flexion angle of about 75 degrees), and a third portion 54 (e.g., corresponding to a flexion angle of about 90 degrees). During use, a patellar component 250 implanted on the patella encounters the first portion 50 of the transition region 66 during the first stage of the 3-stage process. In the second stage of the 3-stage process, the patellar component 250 encounters the second portion 52 of the transition region 66. Finally, in the third stage of the 3-stage process, the patellar component 250 encounters the third portion 54 of the transition region 66. The flexion angles selected for the portions 50, 52, 54 of the transition region 66 are exemplary only. In practice, the prosthetic device can be configured such that the patellar component encounters the portions 50, 52, 54 of the transition region 66 at flexion angles best suited to the patient's unique anatomy.

In this embodiment, in the first stage, as shown in FIG. 10(a), as the patient moves the joint from extension to flexion, the patellar component 250 contacts only the patellofemoral component 14 in the first portion 50 of the transition region 66. In the second stage, the patellar component 250 simultaneously contacts the patellofemoral component 14 and both condyles in the second portion 52 of the transition region 66. If a femoral condyle has been resurfaced with an implant component, the patellar component 250 contacts the implant component (e.g., the component 10 or the component 12). If the condyle is healthy and has not been resurfaced, the patellar component contacts the healthy condyle (e.g., bone and/or cartilage). Thus, in the second stage, the patellar component contacts at least the patellofemoral component 14 and a condyle component (e.g., the component 10 and/or the component 12) in the second portion 52 of the transition region 66. In the case of a tricompartmental implant, in the second stage, the patellar component 250 contacts the patellofemoral component 14 and both condyle components 10 and 12, as shown in FIG. 10(b). In the case of a bicompartmental implant where only one condyle is resurfaced, in the second stage, the patellar component contacts the patellofemoral component 14, one condyle component (e.g., the component 10 or the component 12), and one healthy condyle. In the third stage, the patellar component 250 does not contact the patellofemoral component 14 in the third portion 54 of the transition region 66. For example, for a tricompartmental implant, in the third stage, the patellar component 250 contacts only the condyle components 10 and 12, as shown in FIG. 10(c). For a bicompartmental implant, in the third stage, the patellar component contacts one condyle component (e.g., the component 10 or the component 12) and one healthy condyle. Although the transition region 66 includes three distinct stages and component configurations (e.g., as shown in FIGS. 10(a)-10(c)), the transition region 66 may include additional stages and/or component configurations. For example, in transitioning from the first stage to the second stage, the patellar component 250 may contact the patellofemoral component 14 and only one condyle component simultaneously before also coming into contact with the other condyle component.

In one embodiment, the 3-stage patella transition is accomplished by independently controlling the curvilinear pathways (e.g., trochlear sagittal curves) used to construct the articular geometry of the implant components. For example, the patellofemoral component 14 may include a trochlear sagittal curve 64 that is used to construct the geometry of an articular surface 44 of the patellofemoral component 14. Similarly, the femoral condyle component 10 and/or 12 may be represented by a trochlear sagittal curve 62 that represents a patella pathway (the path followed by the apex of the patella as it passes along the femoral condyle components) and thus is not coextensive with, but is used to construct an articular surface 46 of the femoral condyle component 10 and/or 12. As shown in the sagittal view of FIG. 9, the patellofemoral trochlear sagittal curve 64 and the femoral condyle trochlear sagittal curve 62 diverge at a divergence point 42. At the divergence point 42, the patellofemoral trochlear sagittal curve 64 recesses and sinks deeper than the trochlear sagittal curve 62 used to create the femoral condyle component 10 and/or 12. Thus, the transition region 66 includes the divergence point 42 at which the articular surface 44 of the patellofemoral component 14 diverges superiorly away from the articular surface 46 of the condyle component 10 and/or 12. This divergence enables contact with the patellar component to be transferred from the patellofemoral component 14 to the condyle components 10 and 12, as shown in FIGS. 10(a)-10(c). The divergence point signifies the end of the second stage of the 3-stage process and the beginning of the third stage. The location where the trochlear sagittal curves diverge and the radius of the divergence can be parametrically modified to obtain the desired transition. In a preferred embodiment, the divergence point 42 is located within the transition region 66 and more preferably is located at approximately a midpoint of the transition region 66, i.e., the trochlear sagittal curve 64 diverges or recesses near the middle of the transition region 66. It is within the transition region 66 where the patellar component transition may occur for optimal smoothness.

Figure 9:
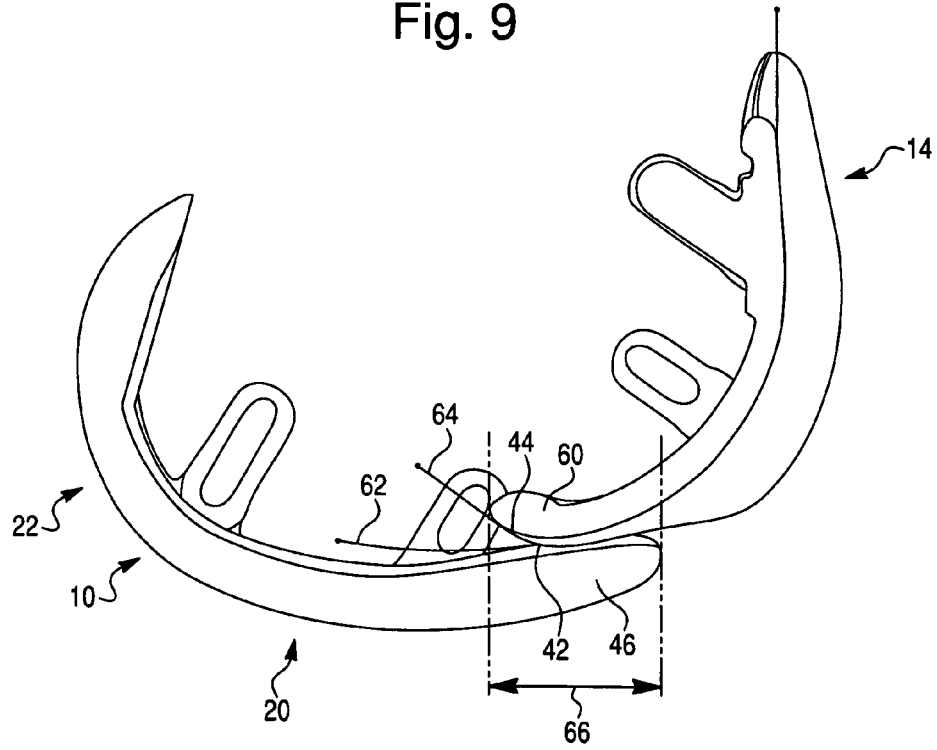
FIG. 9 is a partial cross sectional view of a patella transition according to an embodiment of the present invention.

As shown in FIG. 9, the divergence of the patellofemoral sagittal curve 64 creates a "curled" feature 60. In a preferred embodiment, the feature 60 has radii of at least 6-20 mm. Also, FIG. 9 shows that the condyle component 10 and/or 12 has an anterior portion 20 with a first radius and a posterior portion 22 with a second radius that is less than the first radius. For example, the first radius can be greater than about 30 mm and the second radius can be within the range of about 15 to 30 mm. The transition region 66 (e.g., the transition regions 36, 56) may include one divergence point or multiple divergence points. For example, in one embodiment, the transition region 36 includes a first divergence point at which the articular surface 44 of the patellofemoral component 14 diverges superiorly away from an articular surface of the condyle component 12, and the transition region 56 includes a second divergence point at which the articular surface 44 of the patellofemoral component 14 diverges superiorly away from an articular surface of the second condyle component 10. One advantage of the transition region and trochlear sagittal curve divergence is that, when the trochlear sagittal curve 64 divergence occurs within the transition region 66, the implant components 10, 12, and/or 14 can be slightly positioned away from their ideal locations and still provide a smooth transition for the patellar component 250. As a result, the implant components have a positioning tolerance that enables intra-operative flexibility to independently position each component within a reasonable limit or envelope to ideally match the components to the specific patient geometry for a custom fit using standardized component sizes. Additionally, the positioning tolerance also allows for slight malpositioning due to surgical error (e.g., user error, registration error, etc.).

According to an embodiment, the patellofemoral component 14 and the femoral condyle components 10 and 12 are configured to accommodate a shape of a patellar component. In this embodiment, the components 10, 12, 14 can include articular surfaces shaped to accept a corresponding portion of the patellar component. For example, FIGS. 10(*a*)-10(*c*) illustrate a 3-stage patella transition for a dome-shaped (or semispherical) patellar component 250 where FIG. 10(*a*) shows the patellar component 250 being only centrally supported by the patellofemoral component 14 (e.g., stage one at 60 degrees of flexion), FIG. 10(*b*) shows the patellar component 250 being fully supported by the patellofemoral component 14 and the condyle components 10 and 12 (e.g., stage two at 75 degrees of flexion), and FIG. 10(*c*) shows the patellar component 250 being supported only by the condyle components 10 and 12 (e.g., stage three at 90 degrees of flexion). For dome-shaped patellar components, the main articular surface of the patellar component 250 is convex, as shown in FIGS. 10(*a*)-10(*c*). Since the main articular surface of the patellar component 250 has a sufficiently large and constant shape from the center to outer edge, the patellofemoral and femoral condyle components may share the same complimentary shape to accept the patellar component. For example, the patellofemoral and femoral condyle components may each have a concave region to accept the dome-shaped patellar component 250. For the patellofemoral component 14, the concave trochlear groove 33 can accept the patellar component 250. The shape of the articular surface of the femoral condyle components, however, may be primarily convex. To enable the femoral condyle components to accept the dome-shaped patellar component 250, the femoral condyle components can include a relief in the femoral articular surface. For example, FIGS. 11(*a*) and 11(*b*) show that the condyle component 10 and/or 12 includes a relief 48 configured to accept a portion of a patellar component. FIG. 11(*a*) shows a cross sectional view of the relief 48, which includes small regions of concavity in the condyle component to accommodate the patellar component. FIG. 11(*b*) shows a front view showing the concave shape comprising the relief 48.

The shape of the relief may be adapted for various patellar components. As shown in FIGS. 11(*a*) and 11(*b*), for dome-shaped patellar components, the relief may have a concave shape. In contrast, to accommodate substantially v-shaped (or conical) patellar components, which have a main articular surface that is substantially flat, the relief may comprise a flat region in the articular surface of the condyle component 10 and/or 12 to accept a portion of a v-shaped patellar component.

FIGS. 12(*a*)-12(*c*) show another embodiment of the patellar component transition in which the patellar component 250 is a sombrero-type (or substantially Gaussian-shaped) patellar component. FIG. 12(*a*) shows the patellar component 250 being only centrally supported by the patellofemoral component 14 (e.g., stage one at 60 degrees of flexion), FIG. 12(*b*) shows the patellar component 250 being fully supported by the patellofemoral component 14 and the condyle components 10 and 12 (e.g., stage two at 75 degrees of flexion), and FIG. 12(*c*) shows the patellar component 250 being supported only by the condyle components 10 and 12 (e.g., stage three at 90 degrees of flexion).

The main articular surface of the sombrero-type patellar component 250 has a convex central region and a concave outer region. In general, the patellofemoral component 14 contacts the central convex region, and the femoral condyle component(s) 10 and 12 contact the concave outer region. For this type of patellar component, the complimentary femoral condyle component articular shape to accept the patellar component 250 is convex. Because the femoral condyle components 10, 12 have a generally convex surface shape, a relief is not needed to adapt the condyle components to accept the patellar component.

To install the prosthetic device 5 in the patient, the surgeon preferably uses methods, procedures, and apparatuses as described in U.S. patent application Ser. No. 11/684,514, filed on Mar. 9, 2007, published as U.S. Patent Application Publication 2008/0058945, and incorporated by reference herein in its entirety. The components of the prosthetic device 5 may be implanted in the joint in any known manner, for example, using an adhesive, a cement, an intramedullary rod, a press fit, a mechanical fastener, a projection (e.g., stem, post, spike), and the like. Fixation may also be accomplished via biological or bone in-growth. To promote biological in-growth, the components of the prosthetic device 5 may be coated with hydroxyapatite (HA), have a porous texture (e.g., beads, etc.), include one or more surfaces made from a porous metal (e.g., TRABECULAR METAL ™ currently produced by Zimmer, Inc.), and/or include one or more surfaces having a cellular engineered structure (e.g., TRABECULITE™ currently produced by Tecomet).

In one embodiment, each component of the prosthetic device 5 is implanted using the fixation device best suited for the compartment in which the component will be implanted. For example, the fixation device for a particular component may be selected based on bone quality at the specific site of implantation. For example, if the implantation site has a dense healthy bone, the surgeon may select an implant with a porous coating or porous metal to allow for bone in-growth fixation. The selection of one fixation device or method for one compartment of the joint does not determine the fixation device or method for another compartment. Thus, the components of the prosthetic device 5 may be implanted with similar or different fixation methods and devices.

The components of the prosthetic device 5 may be made of any material or combination of materials suitable for use in an orthopedic implant. Suitable materials include, for example, biocompatible metals (e.g., a cobalt-chromium alloy, a titanium alloy, or stainless steel); ceramics (e.g., an alumina or zirconia-based ceramic); high performance polymers (e.g., ultra-high molecular weight polyethylene); a low friction, low wear polymer/polymer composite; and/or a polymer composite as described in U.S. patent application Ser. No. 10/914,615, U.S. patent application Ser. No. 11/140,775, and/or International Application No. PCT/US2005/028234 (International Pub. No. WO 2006/020619), each of which is hereby incorporated by reference herein in its entirety.

The prosthetic device 5 may include a fixation device configured to be inserted into a bone. For example, the component may include a projection or post 80 for the femur (shown in FIG. 8) and a similar projection on the corresponding tibial component. In another embodiment, a fixation device includes surface features (e.g., projections, keels, fasteners, spikes, biological in-growth sites, etc.) that promote fixation of the component to the bone. In another embodiment, the components of the prosthetic device 5 are configured to be affixed only to an anatomy of the patient (e.g., via press fit, mechanical fastener, adhesive, post, etc.). The component may have a geometry (e.g., as shown in FIG. 8) that corresponds to a geometry of a corresponding surface on the bone. As a result, the component can be press fit to the bone. The corresponding surface on the bone may be, for example, a robotically prepared surface having tolerances engineered to permit the component to be press fit to the surface. The surface may be prepared, for example, as described in U.S. patent application Ser. No. 11/357,197, filed Feb. 21, 2006, published as U.S. Patent Application Publication 2006/0142657, and incorporated by reference herein in its entirety.

According to the embodiments of the present invention, an orthopedic joint prosthesis and techniques that enable customization of implant fit and performance based on each patient's unique anatomy, ligament stability, kinematics, and/or disease state are provided. The above disclosure describes methods and devices that ensure that the transition of the patellar component from one femoral component to another is sufficiently smooth, while at the same time providing some limited inter-component positioning flexibility between the components. Without this smooth transition, the patient may notice the patella transition (sometimes called "patella clunk") and/or the patellar component could wear over time and/or fracture.

The present invention is not limited to the above embodiments. For example, any feature of any embodiment of the prosthetic device may be combined with any other feature of any other embodiment of the prosthetic device, and various combinations among all the features of all the embodiments are contemplated. Furthermore, multiple sizes of the prosthetic devices are possible. Also, bicompartmental embodiments are also contemplated, which may comprise the patellofemoral component 14 and only one of the condyle components, such as the component 10 or the component 12. Alternative embodiments include creating geometry slightly outside the bounds of the preferred embodiments such as making the transition region less than 5 mm or greater than 12 mm, making the gap between the patellofemoral and condyle components greater than 4 mm, making the gap between the patellofemoral and condyle components slightly non-parallel (such as at an angle greater than 20 degrees) to the trochlear groove or the patellar component tracking pathway, and forming the gap between the patellofemoral and condyle components with component edges that are concentric curves having radii of less than 15 mm. The distal curl of the patellofemoral component 14 could be less than 6 mm or greater than 20 mm. A femoral condyle component may be designed to have an anterior tip that is non-articular with the patellofemoral component by removing or recessing the geometry near the anterior tip. The condyle components may or may not include a relief to accept the shape of the patellar component. For some patients, it may be possible to fill the gap between the patellofemoral and condyle components with native tissue to help share the load, such as with existing cartilage or by forming scar tissue. Also, the patellofemoral component, in addition to any combination of the characteristics disclosed above, may include a recess adapted to engage a projection of an opposing component to provide posterior stabilization, as shown in FIG. 4.

Given the disclosure of the present invention, one versed in the art would appreciate that there may be other embodiments and modifications within the scope and spirit of the invention. Accordingly, all modifications attainable by one versed in the art from the present disclosure within the scope and spirit of the present invention are to be included as further embodiments of the present invention. The scope of the present invention is to be defined as set forth in the following claims.

What is claimed is:

1. A prosthetic device configured to form at least a portion of a joint, comprising:
   a plurality of segmented components configured to be fixed relative to a femur of a body including:
      a patellofemoral component; and
      a condyle component,
   wherein each segmented component is configured such that a placement at which the segmented component will be fixed relative to the femur is not constrained by a connection to another of the segmented components that is fixed relative to the femur,
   wherein, in an installed configuration, the patellofemoral and condyle components are configured to be fixed relative to the femur such that:
      a gap is provided in a transverse plane between at least one of:
         (1) a medial edge of the patellofemoral component and an opposing lateral edge of the condyle component, and
         (2) a lateral edge of the patellofemoral component and an opposing medial edge of the condyle component, wherein the gap includes a portion having a substantially uniform width with a midline that is substantially parallel to a trochlear groove of the patellofemoral component, and
      a transition region is provided that extends from a first femoral coronal plane that intersects the patellofemoral component to a second femoral coronal plane that intersects the condyle component, and
      wherein the transition region includes a divergence point at which an articular surface of the patellofemoral component diverges superiorly away from an articular surface of the condyle component, wherein a radius of divergence of the articular surface of the patellofemoral component is at least 6 mm.

2. The prosthetic device of claim 1, wherein the condyle component includes a relief configured to accept a portion of a patellar component.

3. The prosthetic device of claim 1, wherein the midline extends at an angle of less than about 45 degrees relative to the trochlear groove.

4. The prosthetic device of claim 1, wherein the midline extends at an angle of less than about 20 degrees relative to the trochlear groove.

5. The prosthetic device of claim 1, wherein the midline extends at an angle less than about 5 degrees relative to the trochlear groove of the patellofemoral component.

6. The prosthetic device of claim 1, wherein an edge radius of the condyle component, which opposes an edge of the patellofemoral component, is greater than about 15 mm.

7. The prosthetic device of claim 1, wherein the divergence point is located at approximately a midpoint of the transition region.

8. The prosthetic device of claim 1, wherein the gap is less than about 4 mm.

9. The prosthetic device of claim 1, wherein the edge of the patellofemoral component and the opposing edge of the condyle component diverge less than about 20 degrees to provide the substantially uniform width of the gap.

10. The prosthetic device of claim 1, wherein the edge of the patellofemoral component and the opposing edge of the condyle component diverge less than about 10 degrees to provide the substantially uniform width of the gap.

11. The prosthetic device of claim 1, wherein the transition region extends from a location where the first femoral coronal plane intersects the most posterior portion of the patellofemoral component to a location where the second femoral coronal plane intersects the most anterior portion of the condyle component.

12. The prosthetic device of claim 11, wherein a distance between the first and second femoral coronal planes is greater than about 5 mm.

13. The prosthetic device of claim 11, wherein a distance between the first and second femoral coronal planes is greater than about 10 mm.

14. The prosthetic device of claim 11, wherein, during use, a patellar component contacts only the patellofemoral component in a first portion of the transition region, the patellar component contacts at least the patellofemoral component and the condyle component in a second portion of the transition region, and the patellar component does not contact the patellofemoral component in a third portion of the transition region.

15. The prosthetic device of claim 1, wherein the plurality of segmented components includes a second condyle component, and
    wherein, in an installed configuration, the prosthetic device includes a second transition region that extends from the first femoral coronal plane to a third femoral coronal plane that intersects the most anterior portion of the second condyle component, and wherein the second transition region includes a second divergence point at which an articular surface of the patellofemoral component diverges superiorly away from an articular surface of the second condyle component.

16. The prosthetic device of claim 1, wherein the condyle component has an anterior portion with a first radius and a posterior portion with a second radius that is less than the first radius.

17. A prosthetic device configured to form at least a portion of a joint, comprising:
    a plurality of segmented components configured to be fixed relative to a femur of a body including:
        a patellofemoral component; and
        a condyle component,
    wherein each segmented component is configured such that a placement at which the segmented component will be fixed relative to the femur is not constrained by a connection to another of the segmented components that is fixed relative to the femur,
    wherein, in an installed configuration, the patellofemoral and condyle components are configured to be fixed relative to the femur such that:
        a gap is provided between an edge of the patellofemoral component and an opposing edge of the condyle component, wherein the gap includes a portion having a substantially uniform width with a midline that is substantially parallel to a trochlear groove of the patellofemoral component, and
        a transition region is provided that extends from a first femoral coronal plane that intersects the patellofemoral component to a second femoral coronal plane that intersects the condyle component,
    wherein the transition region includes a divergence point at which an articular surface of the patellofemoral component diverges superiorly away from an articular surface of the condyle component, wherein a radius of divergence of the articular surface of the patellofemoral component is at least 6 mm, and
    wherein, during use, a patellar component contacts only the patellofemoral component in a first portion of the transition region, the patellar component contacts at least the patellofemoral component and the condyle component in a second portion of the transition region, and the patellar component does not contact the patellofemoral component in a third portion of the transition region.

18. A prosthetic device configured to form at least a portion of a joint, comprising:
    a plurality of segmented components configured to be fixed relative to a femur of a body including:
        a patellofemoral component; and
        a condyle component, the condyle component including an anterior portion with a first radius and a posterior portion with a second radius that is less than the first radius,
    wherein each segmented component is configured such that a placement at which the segmented component will be fixed relative to the femur is not constrained by a connection to another of the segmented components that is fixed relative to the femur,
    wherein, in an installed configuration, the patellofemoral and condyle components are configured to be fixed relative to the femur such that:
        a gap is provided between an edge of the patellofemoral component and an opposing edge of the condyle component, wherein the gap includes a portion having a substantially uniform width with a midline that is substantially parallel to a trochlear groove of the patellofemoral component, and
        a transition region is provided that extends from a first femoral coronal plane that intersects the patellofemoral component to a second femoral coronal plane that intersects the condyle component, and
    wherein the transition region includes a divergence point at which an articular surface of the patellofemoral component diverges superiorly away from an articular surface of the condyle component, wherein a radius of divergence of the articular surface of the patellofemoral component is at least 6 mm.

\* \* \* \* \*